(12) United States Patent
Chao et al.

(10) Patent No.: US 11,712,696 B2
(45) Date of Patent: Aug. 1, 2023

(54) DRUG SCREENING PLATFORM SIMULATING HYPERTHERMIC INTRAPERITONEAL CHEMOTHERAPY

(71) Applicant: NATIONAL TSING HUA UNIVERSITY, Hsinchu (TW)

(72) Inventors: Te-Yu Chao, New Taipei (TW); Yu-Ching Tung, Taoyuan (TW); Mao-Chih Hsieh, Taipei (TW); Yu-Ting Tai, Taipei (TW); Bing-Ying Ho, Taipei (TW); Wei-Chia Chang, New Taipei (TW); Sung-Yang Wei, New Taipei (TW); Chang-Hung Hsieh, New Taipei (TW); Chung-Cheng Chou, Taoyuan (TW); Jen-Tsan Chi, Chapel Hill, NC (US); Long Hsu, Hsinchu (TW); Hwan-You Chang, Hsinchu (TW); Huang-Ming Philip Chen, Zhubei (TW); Cheng-Hsien Liu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 237 days.

(21) Appl. No.: 17/394,880

(22) Filed: Aug. 5, 2021

(65) Prior Publication Data
US 2022/0401956 A1 Dec. 22, 2022

(30) Foreign Application Priority Data
Jun. 18, 2021 (TW) .................................. 110122422

(51) Int. Cl.
*C12N 15/10* (2006.01)
*B01L 3/00* (2006.01)
(Continued)

(52) U.S. Cl.
CPC ... *B01L 3/502753* (2013.01); *B01L 3/502715* (2013.01); *C12M 23/16* (2013.01);
(Continued)

(58) Field of Classification Search
CPC .............. B01L 3/523; B01L 2300/048; B01L 2300/0663; B01L 2300/14;
(Continued)

(56) References Cited

U.S. PATENT DOCUMENTS

2008/0108121 A1* 5/2008 Liu ...................... C12N 5/0697
435/173.9

FOREIGN PATENT DOCUMENTS

| TW | I412742 B | 9/2006 |
|----|-----------|--------|
| TW | I335936 B | 1/2011 |

* cited by examiner

*Primary Examiner* — Jennifer Wecker
*Assistant Examiner* — Oyeleye Alexander Alabi
(74) *Attorney, Agent, or Firm* — Birch, Stewart, Kolasch & Birch, LLP

(57) ABSTRACT

A drug screening platform simulating hyperthermic intraperitoneal chemotherapy including a dielectrophoresis system, a microfluidic chip and a heating system is disclosed. The dielectrophoresis system is used to provide a dielectrophoresis force. The microfluidic chip includes a cell culture array and observation module and a drug mixing module. The cell culture array and observation module are used to arrange the cells into a three-dimensional structure through the dielectrophoresis force to construct a three-dimensional tumor microenvironment. The drug mixing module is coupled to the cell culture array and observation module and used to automatically split and mix the inputted drugs and output the drug combinations into the cell culture array and observation module. The heating system is used for real-time temperature sensing and heating control of the drug combinations on the microfluidic chip to simulate high-
(Continued)

temperature drug environment when performing hyperthermic intraperitoneal chemotherapy on the three-dimensional tumor microenvironment.

10 Claims, 8 Drawing Sheets

(51) Int. Cl.
G01N 21/3504 (2014.01)
G01N 33/00 (2006.01)
G01N 33/574 (2006.01)
G01N 21/64 (2006.01)
A61K 45/06 (2006.01)
G01N 21/35 (2014.01)
G01N 33/50 (2006.01)
G01N 33/543 (2006.01)
B01L 3/02 (2006.01)
G01N 33/53 (2006.01)
C12N 5/09 (2010.01)
C12N 5/00 (2006.01)
C12M 1/12 (2006.01)
C12M 3/06 (2006.01)
C12M 1/36 (2006.01)

(52) U.S. Cl.
CPC ............ *C12M 25/14* (2013.01); *C12M 41/48* (2013.01); *C12N 5/0068* (2013.01); *C12N 5/0693* (2013.01); *B01L 2300/0645* (2013.01); *B01L 2300/0819* (2013.01); *B01L 2300/0883* (2013.01); *B01L 2400/0424* (2013.01); *C12N 2513/00* (2013.01); *C12N 2533/54* (2013.01)

(58) Field of Classification Search
CPC ....... B01L 2400/0487; B01L 2400/082; B01L 2200/146; B01L 2400/0457; B01L 3/52; G01N 2030/027
See application file for complete search history.

DM

CI

27

27

DRUG SCREENING PLATFORM SIMULATING HYPERTHERMIC INTRAPERITONEAL CHEMOTHERAPY

BACKGROUND OF THE INVENTION

1. Field of the Invention

The invention relates to drug screening; in particular, to a drug screening platform simulating hyperthermic intraperitoneal chemotherapy.

2. Description of the Prior Art

In recent years, the development of Hyperthermic Intraperitoneal Chemotherapy (HIPEC) has gradually received attention, which can combine the effects of hyperthermia and chemotherapeutic drugs to kill microscopic cancer tumor cells in the abdominal cavity. However, there are more than ten drug options for hyperthermic chemotherapy. Therefore, how to choose the best drug combination becomes a key to the success of this therapy.

Conventionally, thermochemotherapy drugs are often selected by doctors based on their practical experience. However, due to the individual differences of different patients, it often leads to the use of the same drug to produce different degrees of curative effect, and conventionally most of the thermochemotherapeutic drug screenings are carried out manually using orifice plates and culture plates, which are less suitable for the simulation of the temperature-controlled intraperitoneal thermochemotherapy environment. As a result, the screening of intraperitoneal thermochemotherapy drugs forms a bottleneck to patient treatment progress which leads to delays and waste of medical resources, and it requires further improvement to achieve the goal of precision drug.

SUMMARY OF THE INVENTION

Therefore, the invention provides a drug screening platform simulating hyperthermic intraperitoneal chemotherapy to solve the above-mentioned problems of the prior arts.

One of the scopes of the invention is to propose a drug screening platform simulating the environment of intraperitoneal thermochemotherapy, which uses microfluidic technology to establish an automatic drug combination and mixing system with three-dimensional cell culture technology, and combined with a heating control system to solve the clinical problem that the selection of intraperitoneal thermochemotherapy drugs is difficult, so it can provide doctors and patients with reference when choosing drugs to achieve the goal of precision drug.

Another scope of the invention is to propose a microfluidic drug screening platform, which uses geometric design, fluid dynamics calculations and microelectromechanical process technology to achieve the combination of cell culture, multiple drug permutations and combinations, cell death and alive detection, and temperature control. The goal of the platform is to realize the effect of inputting three to four drugs through the geometric logic design of the microfluidic channel and automatically outputting up to ten drug combinations; its microstructure design allows cancer cell culture to be carried out directly on this platform.

A preferred embodiment of the invention is a drug screening platform simulating hyperthermic intraperitoneal chemotherapy. In this embodiment, the drug screening platform simulating hyperthermic intraperitoneal chemotherapy includes a dielectrophoresis system, a microfluidic chip and a heating system. The dielectrophoresis system is configured to provide a dielectrophoresis force. The microfluidic chip includes a cell culture array and observation module and a drug mixing module. The cell culture array and observation module is configured to arrange the cells into a three-dimensional structure through the dielectrophoresis force to construct a three-dimensional tumor microenvironment. The drug mixing module is coupled to the cell culture array and observation module and configured to automatically split and mix the inputted drugs and output the drug combinations into the cell culture array and observation module. The heating system is configured to perform real-time temperature sensing and heating control on the drug combinations on the microfluidic chip to simulate high-temperature drug environment when performing hyperthermic intraperitoneal chemotherapy on the three-dimensional tumor microenvironment.

In an embodiment, the microstructure of the microfluidic chip combined with the three-dimensional light-curing hydrogel system or collagen constructs a three-dimensional bionic cell culture environment to simulate the growth of tumors in the body.

In an embodiment, when the hydrogel of the three-dimensional light-curing hydrogel system is solidified, the excess hydrogel and cells are rinsed through the buffer, and the cell culture array and observation module includes a micro-pillar structure to prevent the solidified hydrogel and cells from being washed away.

In an embodiment, the drug screening platform for simulating intraperitoneal hyperthermia chemotherapy also includes an automatic perfusion system for automatically perfusing the multiple drug combinations to the cell culture array and observation module to simulate the perfusion environment when performing intraperitoneal hyperthermia chemotherapy on the three-dimensional tumor microenvironment.

In an embodiment, the dielectrophoresis system includes dielectrophoresis electrodes. The dielectrophoresis electrode has a specific pattern. When the dielectrophoresis electrode is energized, the dielectrophoresis force is generated to automatically push the cell mixture to the cell culture array and observation module, and perform subsequent cell culture.

In an embodiment, the heating system includes a heating device, a temperature sensing device and a temperature control device. The heating device heats the microfluidic chip to the setting temperature, and feedback control is performed by the temperature sensing device and the temperature control device to achieve real-time heating control.

In an embodiment, the microfluidic chip also includes a cell injection module, which is coupled to the cell culture array and the observation module, and is configured to inject the cell mixture and evenly distribute it to provide a plurality of cell culture arrays and observation modules.

In an embodiment, the microfluidic chip has a dual-layer structure. The upper structure of the dual-layer structure includes a cell injection module and a drug mixing module, and the lower structure of the dual-layer structure includes a cell culture array and an observation module.

In an embodiment, the drug mixing module also includes a curved flow channel and a micro-mixer structure. The curved channel is configured to control the flow resistance and the micro-mixer structure is configured to help drug mixing.

In an embodiment, the drug mixing module also includes a plurality of drug input terminals and a control group medium input terminal. The plurality of drug input terminals is configured to input a plurality of drugs, and the control group medium input terminal is configured to input culture medium for the control group.

Compared to the prior art, the invention provides a drug combination screening platform capable of simulating the high-temperature drug perfusion environment of intraperitoneal hyperthermia chemotherapy, which can have the following advantages/effects:

(1) three-dimensional tumor microenvironment construction: using the microstructure of the microfluidic chip, with a three-dimensional light-curing hydrogel system or collagen, a three-dimensional bionic cell culture environment can be constructed to simulate the growth of tumors in human body.

(2) drug combination screening array: the microfluidic chip design can automatically split the input drugs, output a single drug or a combination of multiple drugs after mixing, and perform drug screening tests at the same time.

(3) simulating the environment of intraperitoneal thermochemotherapy: the heating system of this platform can realize real-time temperature sensing and heating control, so as to heat the drug on the chip to the temperature commonly used for intraperitoneal thermochemotherapy, and it is directly perfused by the automatic perfusion system to the three-dimensional cell culture array of the chip to simulate the treatment situation during intraperitoneal hyperthermia chemotherapy.

(4) application of dielectrophoresis force: this platform also combines the design of dielectrophoresis electrodes; when the electrodes are energized, the cell mixture can be automatically pushed to the target area (that is, the cell culture array area) by using the dielectrophoresis force and the electrode patterns are arranged into a designed shape for subsequent cell culturing.

The advantage and spirit of the invention may be understood by the following detailed descriptions together with the appended drawings.

BRIEF DESCRIPTION OF THE APPENDED DRAWINGS

FIG. 1 and FIG. 2 respectively illustrate a functional block diagram and a schematic diagram of a screening platform for intraperitoneal hyperthermia chemotherapy drugs in a preferred embodiment of the invention.

Figure 6:
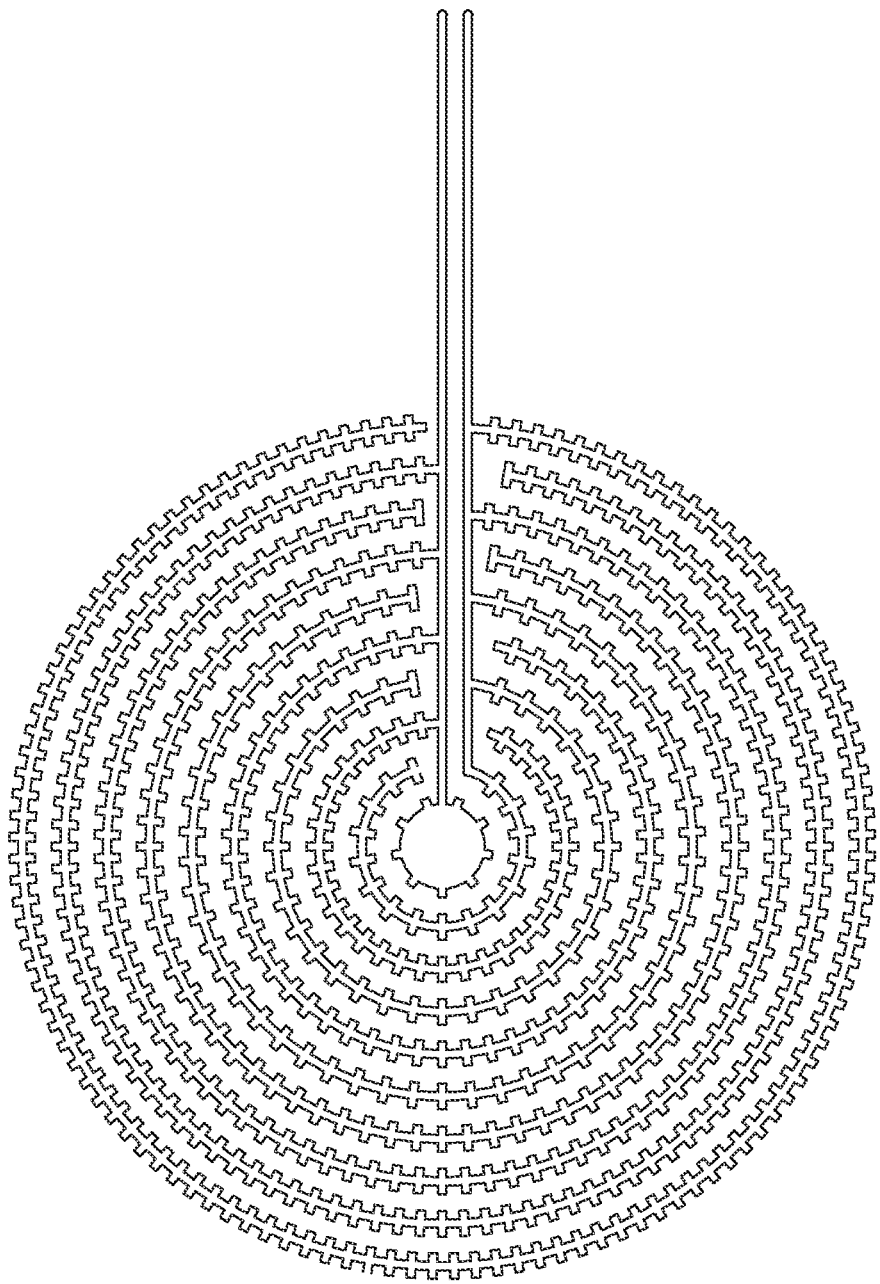
Figure 7:
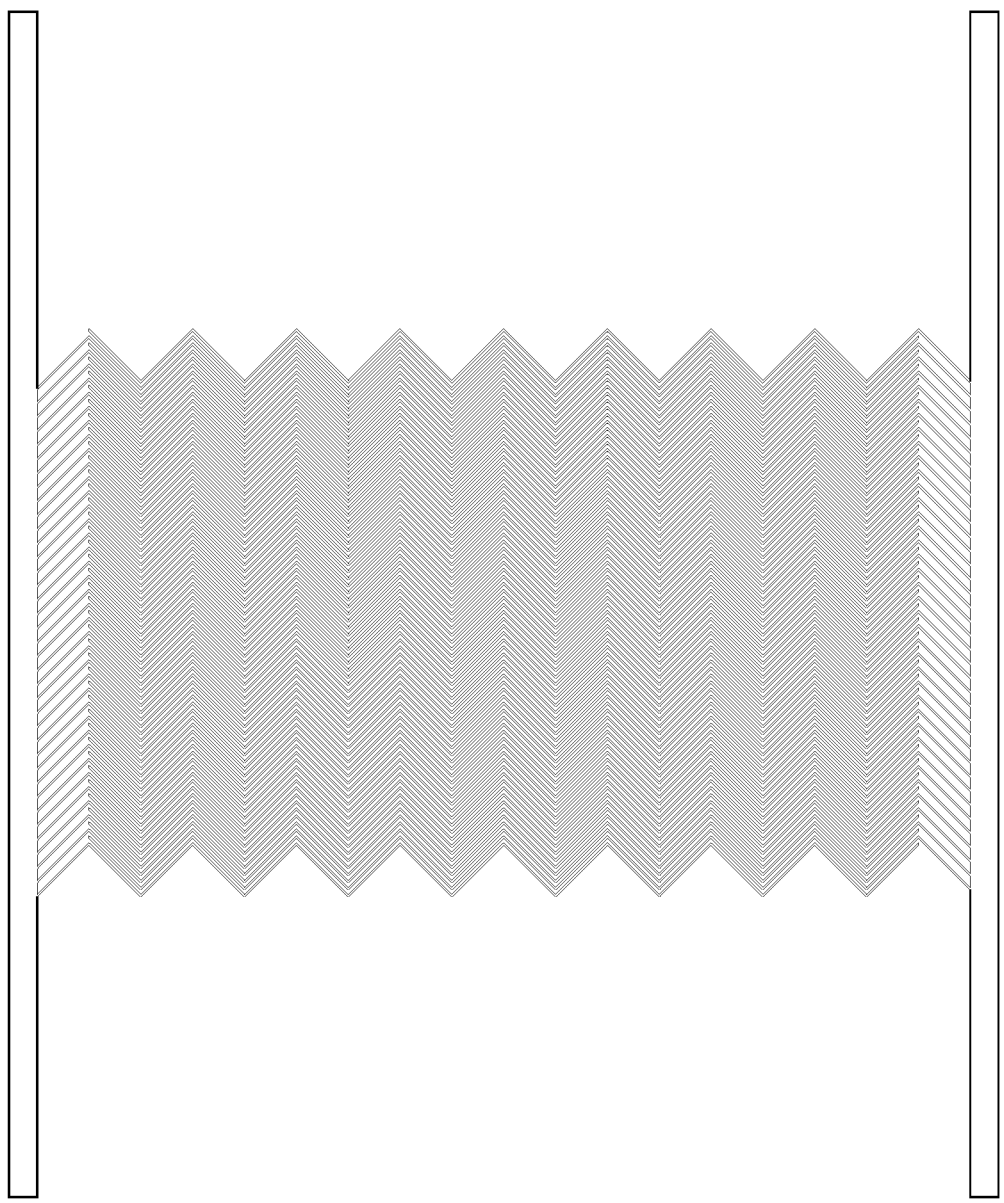

FIG. 6 and FIG. 7 respectively illustrate schematic diagrams of different embodiments in which the dielectrophoretic electrode structure has a specific pattern.

Figure 8A:
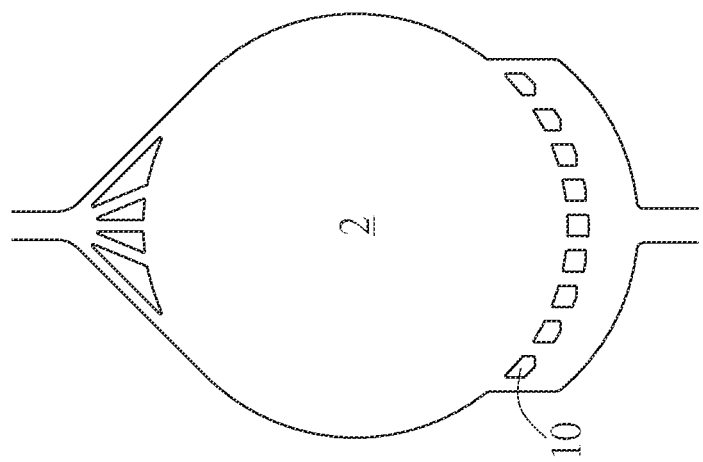
Figure 8B:
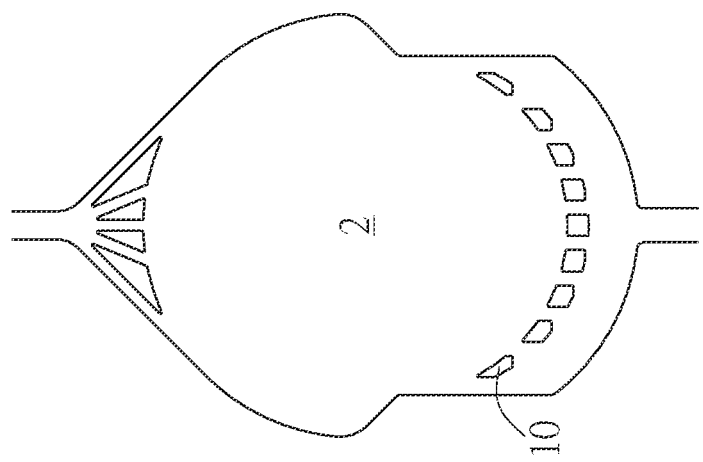
Figure 8C:
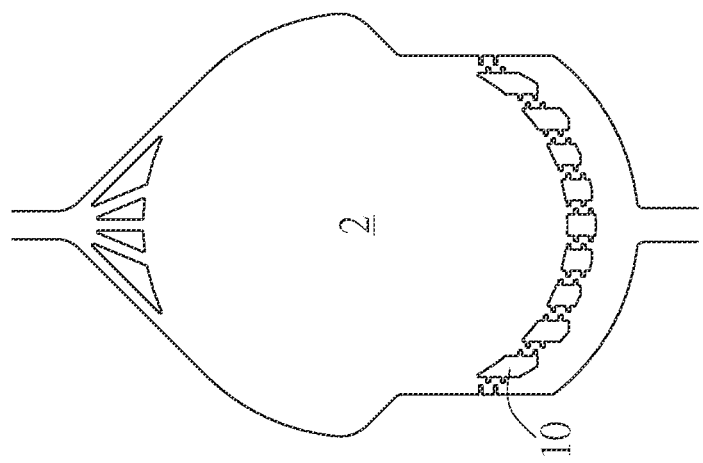

FIG. 8A-FIG. 8C illustrate schematic diagrams of different embodiments in which the cell culture array and observation module includes micro-pillar structures respectively.

DETAILED DESCRIPTION OF THE INVENTION

Reference will now be made in detail to the exemplary embodiments of the invention, and examples of the exemplary embodiments are illustrated in the drawings. Elements/components with the same or similar numbers used in the drawings and embodiments are used to represent the same or similar parts.

A specific embodiment of the invention is a drug screening platform simulating intraperitoneal hyperthermia chemotherapy, which uses microfluidic technology to establish an automated drug combination mixing system, with three-dimensional cell culture technology, and combined with a heating control system to solve clinical problems. The selection of hyperthermic drugs in the upper abdominal cavity is difficult to provide a reference for doctors and patients when choosing drugs to achieve the goal of precision drug. In addition, the drug screening platform simulating intraperitoneal hyperthermia chemotherapy uses geometric design, fluid dynamics calculations, and micro-electromechanical process technology to achieve the goal of combining cell culture, multiple drug permutations and combinations, cell death detection, and temperature control on the same platform, and the geometric logic design of the microfluidic channel can realize the effect of inputting three to four drugs and automatically outputting up to ten drug combinations. Through the microstructure design, the cancer cell culture can be directly carried out on this platform.

Figure 1:
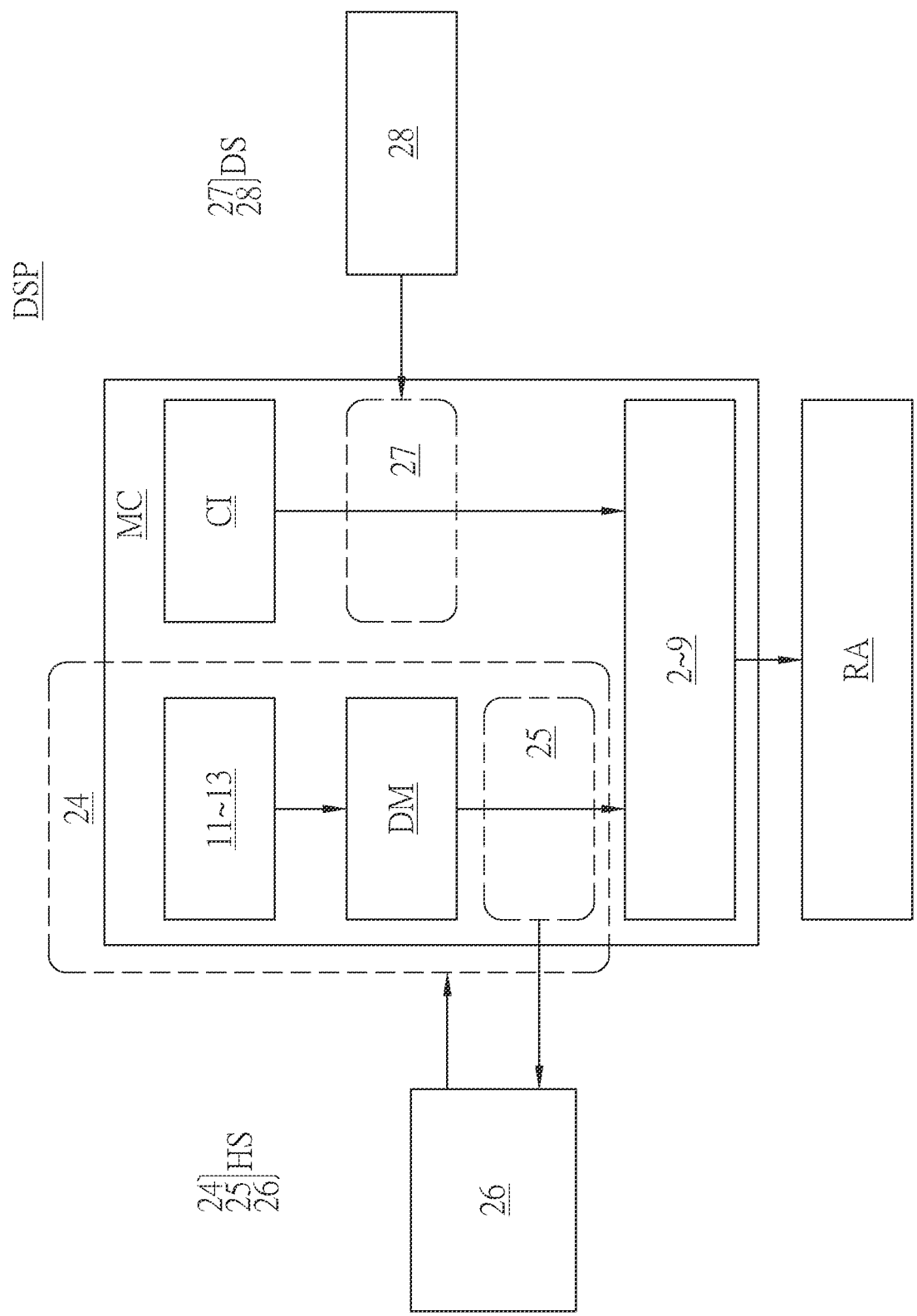
Figure 2:
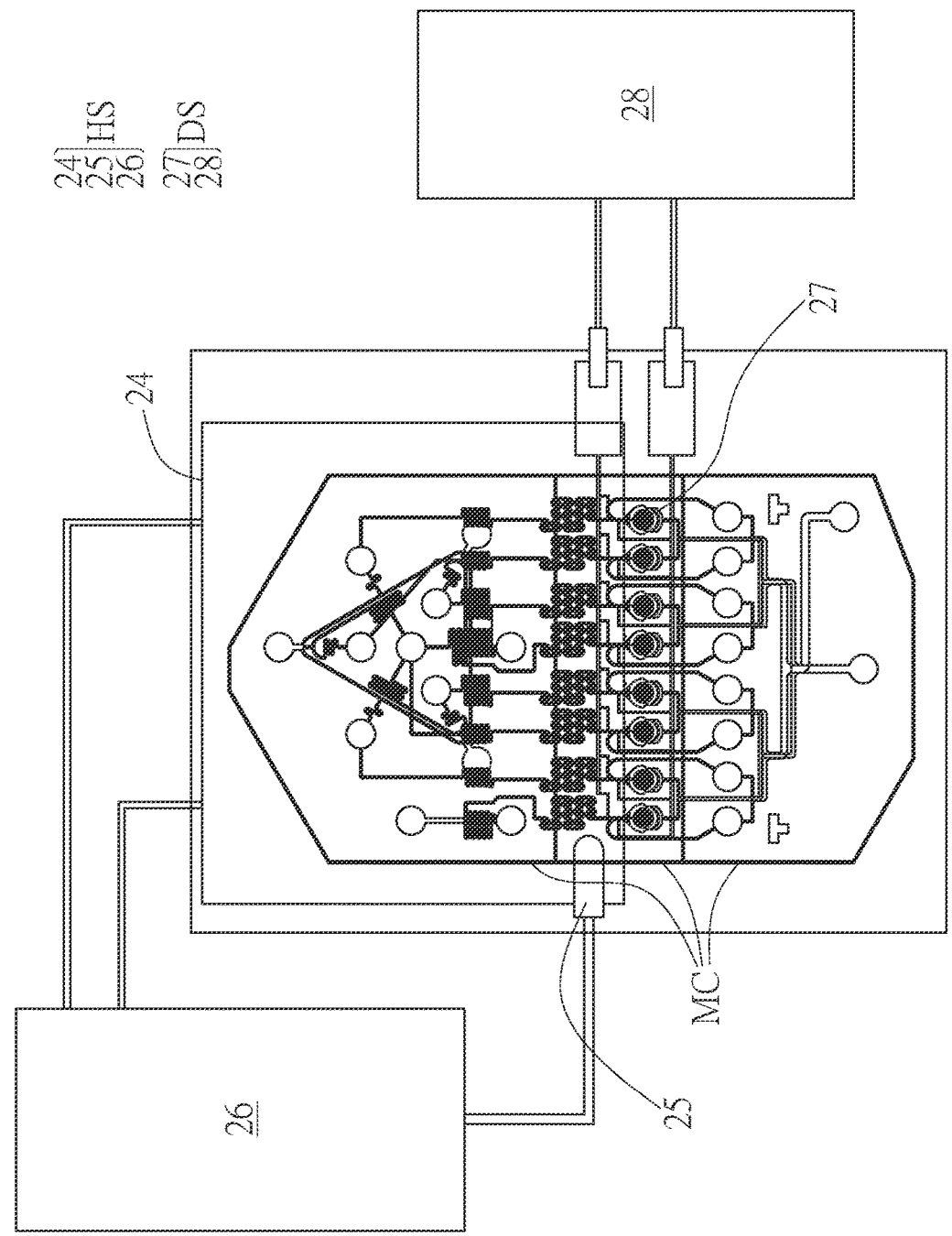
Figures 3A, 3B:
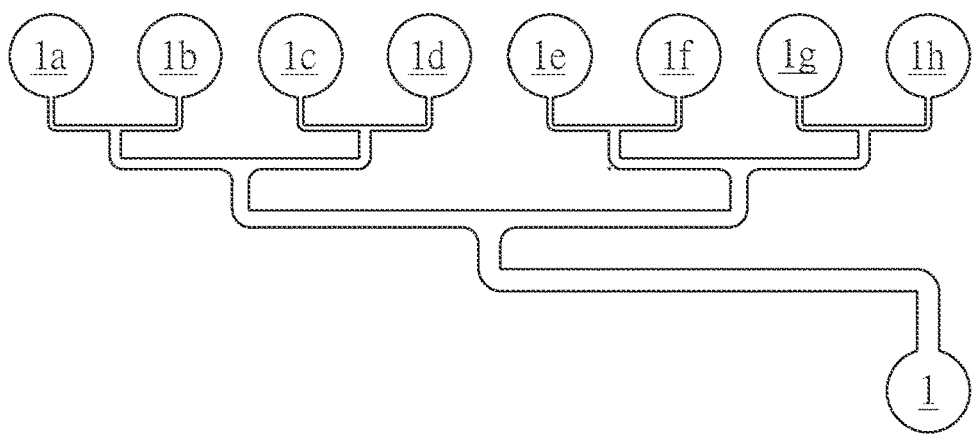
FIG. 3A illustrates a schematic diagram of the drug mixing module in the upper layer structure of the microfluidic chip.
FIG. 3B illustrates a schematic diagram of the cell injection module in the upper structure of the microfluidic chip.
Figure 4:
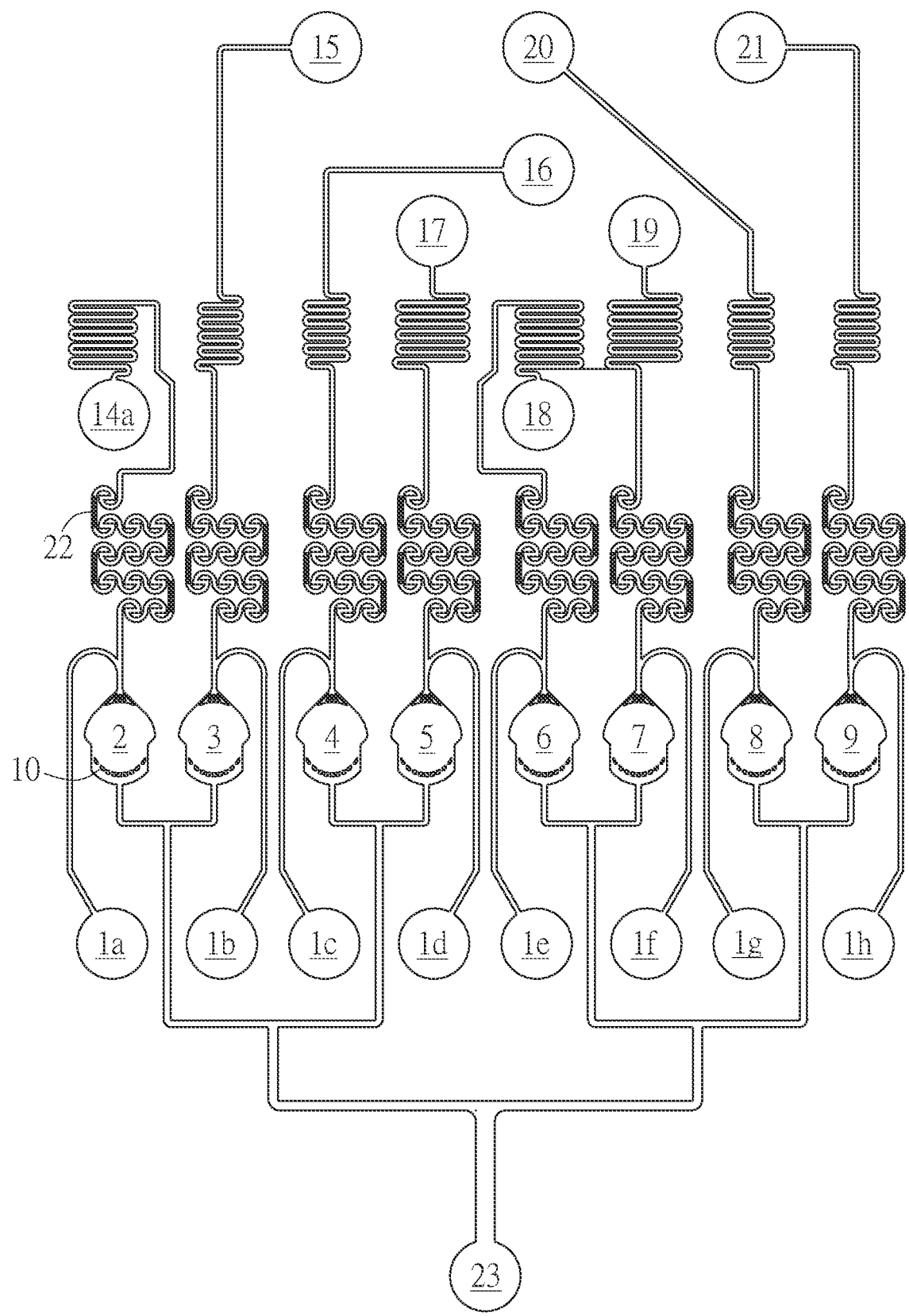
FIG. 4 illustrates a schematic diagram of the cell culture array and the observation modules in the lower structure of the microfluidic chip.
Figure 5:
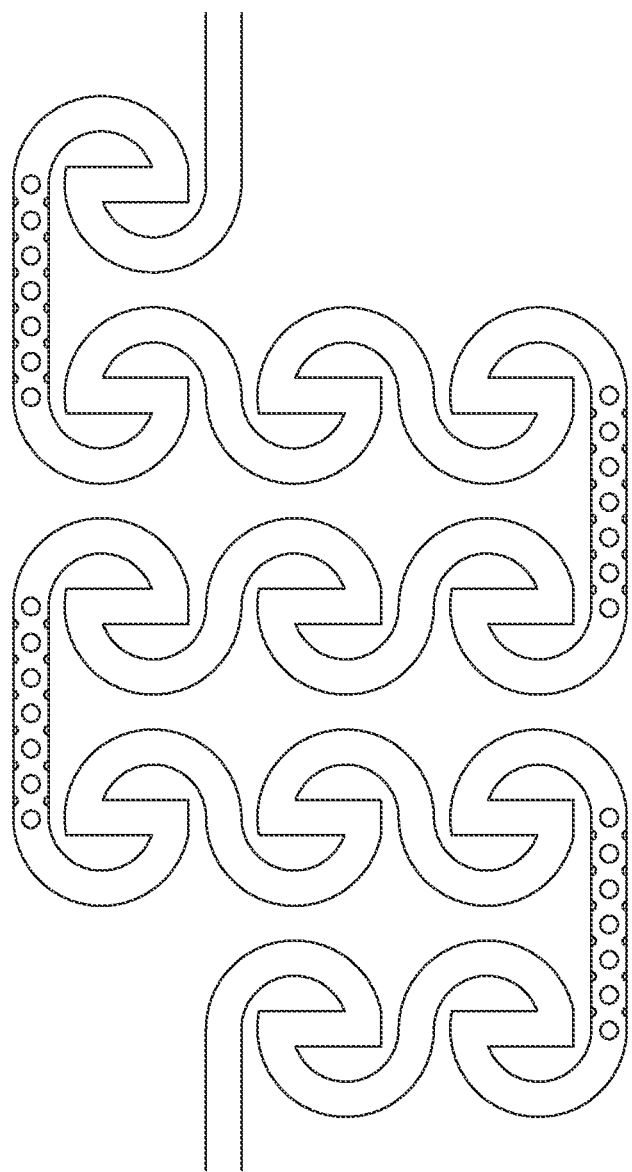
FIG. 5 illustrates a schematic diagram of the micro-mixer structure.

Next, please refer to FIG. 1 to FIG. 8C. FIG. 1 illustrates the functional block diagram of the intraperitoneal thermochemotherapy drug screening platform DSP in this embodiment; FIG. 2 illustrates the schematic diagram of the intraperitoneal thermochemotherapy drug screening platform DSP in this embodiment; FIG. 3A illustrates a schematic diagram of the drug mixing module DM in the upper layer structure of the microfluidic chip MC; FIG. 3B illustrates a schematic diagram of a cell injection module CI located at the upper structure of the microchannel chip MC; FIG. 4 illustrates a schematic diagram of the cell culture array and the observation modules 2~9 in the lower structure of the microfluidic chip MC; FIG. 5 illustrates a schematic diagram of the micro-mixer structure 22; FIG. 6 and FIG. 7 respectively illustrate schematic diagrams of different embodiments in which the structure of the dielectrophoresis electrode 27 has a specific pattern; FIG. 8A~FIG. 8C illustrate schematic diagrams of different embodiments in which the cell culture array and the observation module include micro-pillar structures respectively.

In this embodiment, the drug screening platform DSP simulating intraperitoneal thermochemotherapy includes a dielectrophoresis system DS, a microfluidic chip MC and a heating system HS.

The dielectrophoresis system DS is used to provide dielectrophoresis power. The dielectrophoresis system DS includes a dielectrophoresis electrode 27. The structure of the dielectrophoresis electrode 27 can have a specific pattern, as shown in FIG. 6 and FIG. 7, but not limited to this. When the dielectrophoresis electrode 27 is energized, a dielectrophoresis force is generated to automatically push the cell mixture to the cell culture array and observation modules 2~9, and then subsequent cell culturing will be performed.

The microfluidic wafer MC has a dual-layer structure. An upper structure of the dual-layer structure includes a cell injection module CI and a drug mixing module DM, and a lower structure of the dual-layer structure includes cell culture array and observation modules 2~9. The cell injection module CI is coupled to the cell culture array and observation modules 2~9. The drug mixing module DM is coupled to the cell culture array and observation modules 2~9. The cell culture array and observation modules 2~9 can be coupled to the result analysis device RA.

The cell injection module CI includes a cell injection terminal 1 and a plurality of cell output terminals 1a~1h. The mixed solution of cells and hydrogel is injected from the cell injection terminal 1 and can be automatically evenly distributed to the plurality of cell output terminals 1a~1h through the geometric design of microfluidic channel, so as to be provided to a plurality of cell culture array and observation models 2~9 respectively.

The plurality of cell culture array and observation modules 2~9 is used to arrange the plurality of cells in the cell mixture into a three-dimensional structure through the dielectrophoresis force to construct a three-dimensional tumor microenvironment. It should be noted that the microstructure of the microfluidic chip MC can be combined with a three-dimensional light-curing hydrogel system or collagen to construct a three-dimensional bionic cell culture environment to simulate the growth of tumors in a body.

After the hydrogel of the three-dimensional light curing hydrogel system is solidified, excess hydrogel and cells can be washed away through a buffer and then outputted from the waste liquid recycling terminal 23. The cell culture array and observation modules 2~9 can include a micro-pillar structure 10 to prevent the solidified hydrogel and cells from being washed away. As for the different embodiments of the cell culture array and observation modules 2~9 including the micro-pillar structure 10, please refer to FIG. 8A~FIG. 8C.

The drug mixing module DM is used to automatically split and mix the input multiple drugs and then output the multiple drug combinations to the cell culture array and observation modules 2~9 respectively. It should be noted that the drug mixing module DM includes a plurality of drug input terminals 11-13, a control group medium input terminal 14, a drug combination output unit 15-21 and a micro-mixer structure 22.

After the cells are fixed on the microfluidic chip, the pump automatic perfusion system can be used to input a plurality of drugs from the plurality of drug input terminals 11~13 and input the control group from the control group medium input terminal 14. The geometric design of the drug mixing module DM can automatically form different drug combinations of the multiple drugs to the drug combination output units 15~21, and then cooperate with the automatic perfusion system to automatically perfuse the multiple drug combinations to the cell culture array and observation modules 2~9 to simulate the perfusion environment of intraperitoneal hyperthermia chemotherapy for the three-dimensional tumor microenvironment. The micro-mixer structure 22 is used to facilitate the mixing of drugs and can adjust the flow resistance through the curved flow channel.

The heating system HS is used for real-time temperature sensing and heating control of the plurality of drug combinations on the microfluidic chip MC, so as to simulate the high temperature drug environment when performing intraperitoneal thermochemotherapy on the three-dimensional tumor microenvironment. It should be noted that the heating system HS can include a heating device 24, a temperature sensing device 25 and a temperature control device 26. The heating device 24 heats the microfluidic chip MC to a set temperature, and the temperature sensing device 25 and the temperature control device 26 perform feedback control to achieve real-time heating control.

When the simulated three-dimensional tumors are screened for drug combination under the high temperature drug perfusion environment of simulating intraperitoneal hyperthermia chemotherapy, the cell culture array and observation modules 2~9 will transmit the observation results to the result analysis device RA for subsequent analysis to provide analysis results for doctors and patients to refer to when choosing drugs.

Compared to the prior art, the invention provides a drug combination screening platform capable of simulating the high-temperature drug perfusion environment of intraperitoneal hyperthermia chemotherapy, which can have the following advantages/effects:

(1) three-dimensional tumor microenvironment construction: using the microstructure of the microfluidic chip, with a three-dimensional light-curing hydrogel system or collagen, a three-dimensional bionic cell culture environment can be constructed to simulate the growth of tumors in human body.

(2) drug combination screening array: the microfluidic chip design can automatically split the input drugs, output a single drug or a combination of multiple drugs after mixing, and perform drug screening tests at the same time.

(3) simulating the environment of intraperitoneal thermochemotherapy: the heating system of this platform can realize real-time temperature sensing and heating control, so as to heat the drug on the chip to the temperature commonly used for intraperitoneal thermochemotherapy, and it is directly perfused by the automatic perfusion system to the three-dimensional cell culture array of the chip to simulate the treatment situation during intraperitoneal hyperthermia chemotherapy.

(4) application of dielectrophoresis force: this platform also combines the design of dielectrophoresis electrodes; when the electrodes are energized, the cell mixture can be automatically pushed to the target area (that is, the cell culture array area) by using the dielectrophoresis force and the electrode patterns are arranged into a designed shape for subsequent cell culturing.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. A drug screening platform simulating hyperthermic intraperitoneal chemotherapy, comprising:
   a dielectrophoresis system, configured to provide a dielectrophoresis force;
   a microfluidic chip, comprising:
   a cell culture array and observation module, configured to arrange the cells into a three-dimensional structure through the dielectrophoresis force to construct a three-dimensional tumor microenvironment; and
   a drug mixing module, coupled to the cell culture array and observation module and configured to automatically split and mix the inputted drugs and output the drug combinations into the cell culture array and observation module; and
   a heating system, configured to perform real-time temperature sensing and heating control on the drug combinations on the microfluidic chip to simulate high-temperature drug environment when performing hyperthermic intraperitoneal chemotherapy on the three-dimensional tumor microenvironment.

2. The drug screening platform simulating hyperthermic intraperitoneal chemotherapy of claim 1, wherein a microstructure of the microfluidic chip combined with a three-dimensional light-curing hydrogel system or collagen constructs a three-dimensional bionic cell culture environment to simulate a growth of tumors in a body.

3. The drug screening platform simulating hyperthermic intraperitoneal chemotherapy of claim 2, wherein when a hydrogel of the three-dimensional light-curing hydrogel system is solidified, excess hydrogel and cells are rinsed through a buffer, and the cell culture array and observation module comprises a micro-pillar structure to prevent the solidified hydrogel and cells from being washed away.

4. The drug screening platform simulating hyperthermic intraperitoneal chemotherapy of claim 1, further comprising an automatic perfusion system for automatically perfusing the drug combinations to the cell culture array and observation module to simulate a perfusion environment when performing intraperitoneal hyperthermia chemotherapy on the three-dimensional tumor microenvironment.

5. The drug screening platform simulating hyperthermic intraperitoneal chemotherapy of claim 1, wherein the dielectrophoresis system comprises a dielectrophoresis electrode having a specific pattern, when the dielectrophoresis electrode is energized, a dielectrophoresis force is generated to automatically push the cell mixture to the cell culture array and observation module for subsequent cell culturing.

6. The drug screening platform simulating hyperthermic intraperitoneal chemotherapy of claim 1, wherein the heating system comprises a heating device, a temperature sensing device and a temperature control device; the heating device is configured to heat the microfluidic chip to a setting temperature, and feedback control is performed by the temperature sensing device and the temperature control device to achieve real-time heating control.

7. The drug screening platform simulating hyperthermic intraperitoneal chemotherapy of claim 1, wherein the microfluidic chip also comprises a cell injection module, which is coupled to the cell culture array and the observation module and configured to inject the cell mixture and evenly distribute the cell mixture to provide to a plurality of cell culture array and observation modules.

8. The drug screening platform simulating hyperthermic intraperitoneal chemotherapy of claim 7, wherein the microfluidic chip has a dual-layer structure; an upper structure of the dual-layer structure comprises a cell injection module and a drug mixing module, and a lower structure of the dual-layer structure comprises a cell culture array and an observation module.

9. The drug screening platform simulating hyperthermic intraperitoneal chemotherapy of claim 1, wherein the drug mixing module also comprises a curved flow channel and a micro-mixer structure; the curved channel is configured to control flow resistance and the micro-mixer structure is configured to help drug mixing.

10. The drug screening platform simulating hyperthermic intraperitoneal chemotherapy of claim 1, wherein the drug mixing module also comprises a plurality of drug input terminals and a control group medium input terminal; the plurality of drug input terminals is configured to input a plurality of drugs, and the control group medium input terminal is configured to input culture medium used as control group.

* * * * *